(12) United States Patent
Wang

(10) Patent No.: US 8,803,961 B2
(45) Date of Patent: Aug. 12, 2014

(54) MULTI-STREAM IMAGE DECODING APPARATUS AND METHOD

(75) Inventor: Kang-Huai Wang, Saratoga, CA (US)

(73) Assignee: Capso Vision, Inc., Saratoga, CA (US)

( * ) Notice: Subject to any disclaimer, the term of this patent is extended or adjusted under 35 U.S.C. 154(b) by 960 days.

(21) Appl. No.: 12/127,753

(22) Filed: May 27, 2008

(65) Prior Publication Data

US 2009/0299140 A1    Dec. 3, 2009

(51) Int. Cl.
*H04N 7/18* (2006.01)
*A61B 1/00* (2006.01)
*A61B 1/04* (2006.01)
*A61B 5/07* (2006.01)

(52) U.S. Cl.
CPC ............ *H04N 7/185* (2013.01); *A61B 1/00009* (2013.01); *A61B 5/073* (2013.01); *A61B 1/00016* (2013.01); *A61B 1/00036* (2013.01); *A61B 1/041* (2013.01)
USPC .......................................................... 348/77

(58) Field of Classification Search
CPC ........... A61B 1/00009; A61B 1/00016; A61B 1/00025; A61B 1/00036; A61B 1/041; A61B 5/073; H04N 2005/2255
USPC ........................... 600/109; 348/45, 65–70, 77
See application file for complete search history.

(56) References Cited

U.S. PATENT DOCUMENTS 5,604,531 A *  2/1997  Iddan et al. ..................... 348/76
2005/0038321 A1  2/2005  Fujita et al.

FOREIGN PATENT DOCUMENTS

| FR | 2 842 721 | 1/2004 |
|---|---|---|
| GB | 2 307 375 | 5/1997 |
| JP | 2005277740 A | 10/2005 |
| WO | 0165995 A2 | 9/2001 |
| WO | 2007/074445 | 7/2007 |
| WO | 2009146017 A1 | 12/2009 |

OTHER PUBLICATIONS

PCT International Search Report for International Application No. PCT/US2009/038802 dated Jul. 16, 2009, 3 pages.

(Continued)

*Primary Examiner* — Christopher Biagini
(74) *Attorney, Agent, or Firm* — Edward C. Kwok; Hogan Lovells US LLP

(57) ABSTRACT

A capsule camera includes a wireless transmitter that transmits data and a receiving system having multiple receiving units to allowing storing multiple data streams simultaneously. The multiple stored data streams may be used at a later time to derive the best data stream for analysis, based on the network conditions at the time each data packet is received. The best data stream may be derived from the multiple stored data streams at a later time during the decoding process. For example, in a capsule camera application, the multiple data streams may be stored in the memory devices associated with the receiving units, which are typically attached to different locations on the body during diagnosis. The multiple data streams are maintained as the capsule passes through the gastrointestinal tract. Subsequently, after the diagnosis, the receiving units are recovered and connected to a computer or another standalone device for analysis. At that time, the best data stream is derived from the stored data streams using a decoding process, or by comparing the decoded results. Not all receiving units store the data streams at the same time. A screening process, for example, may be provided such that only the receiving units with better network conditions store the data streams. In a real-time system, the data streams may be stored for only a short duration before the best data stream is derived by a decoding process, or by comparing the decoded results.

42 Claims, 18 Drawing Sheets

(56) References Cited

OTHER PUBLICATIONS

PCT Written Opinion of the International Searching Authority for International Application No. PCT/US2009/038802 dated Jul. 16, 2009, 5 pages.

Chinese First Office Action for Application No. 200980129312.X dated Apr. 18, 2012, 5 pgs.

European Written Opinion for Application No. 09755380.4-1241 PCT/US2009038802 dated Jan. 7, 2011, 2 pgs.

PCT Written Opinion for Application No. PCT/US2009038802, 5 pgs.

Japanese Notice of Reasons for Rejection for Application No. 2011-511665, dated Oct. 31, 2013 with English translation, 8 pgs.

* cited by examiner

MULTI-STREAM IMAGE DECODING APPARATUS AND METHOD

BACKGROUND OF THE INVENTION

1. Field of the Invention

The present invention relates to a swallowable capsule camera for imaging of the gastro-intestinal (GI) tract. In particular, the present invention relates to a capsule camera that provides multiple video data stream to multiple receiving units for storage, from which a data stream may be derived for decoding and analysis.

2. Discussion of the Related Art

Devices for imaging body cavities or passages in vivo are known in the art and include endoscopes and autonomous encapsulated cameras. Endoscopes are flexible or rigid tubes that are passed into the body through a body orifice or through a surgical opening, typically into the esophagus via the mouth or into the colon via the rectum. An image is taken at the distal end using a lens and the image data is transmitted to the proximal end outside the body, either by a lens-relay system or by a coherent fiber-optic bundle. A conceptually similar instrument may record an image electronically at the distal end, for example using a CCD or CMOS array, and the image data is then transferred by electrical signal to the proximal end over a cable. The endoscope is an instrument that allows a physician control over its field of view and is a well-accepted diagnostic tool. However, endoscopes have a number of limitations, present risks to the patient, are invasive and are uncomfortable for the patient. The cost of these procedures restricts their application as routine health-screening tools.

Because of the difficulty in traversing a convoluted passage, endoscopes cannot reach most of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily in-patient services that involve a significant amount of time from clinicians and thus are costly.

An alternative in vivo image sensor that addresses many of these problems is capsule endoscopy. In capsule endoscopy, a digital camera is housed in a swallowable capsule, along with a radio transmitter for transmitting image captured by the digital camera. The transmitted image data is received into a base-station receiver or transceiver for recordation in a data recorder outside the body. The capsule camera may also include a radio receiver for receiving instructions or other data from a base-station transmitter. Instead of radio-frequency transmission, lower-frequency electromagnetic signals may be used also. Power to the capsule may be supplied inductively from an external source or by a battery within the capsule.

An early example of a camera in a swallowable capsule is described in U.S. Pat. No. 5,604,531, issued to the Ministry of Defense, State of Israel. A number of patents assigned to Given Imaging (e.g., U.S. Pat. Nos. 6,709,387 and 6,428,469) describe such a system in greater detail. In each of these systems, the capsule camera includes a transmitter for sending the images captured to an external receiver. Other patents issued to Olympus Corporation describe a similar technology. For example, U.S. Pat. No. 4,278,077 discloses a capsule camera for the stomach, which includes film in the camera. U.S. Pat. No. 6,939,292 discloses a capsule with a memory and a transmitter.

An autonomous encapsulated camera with an internal battery has the advantage that the measurements may be made with the patient ambulatory, out of the hospital, and with only moderate restrictions of activity. The base station includes an antenna array that is placed surrounding the bodily region or regions of interest and this antenna array can be temporarily affixed to the skin or can be incorporated into a wearable vest. A data recorder is attached to a belt and includes a battery power supply and data storage medium for saving the images received by the antenna array and any other data transmitted. The stored data is subsequently uploaded onto a diagnostic computer system for analysis.

A typical procedure using such a capsule camera consists of an in-patient visit in the morning during which a clinician attaches the base station apparatus to the patient and the patient swallows the capsule. The system begins recording images just prior to swallowing and continues to record images of the GI tract until the battery completely discharges. Peristalsis propels the capsule through the GI tract. The rate of capsule passage through the GI tract depends on the degree of motility. Usually, the small intestine is traversed in 4 to 8 hours. After a prescribed period, the patient returns the data recorder to the clinician who then uploads the data onto a computer for subsequent viewing and analysis. The capsule is eliminated through the rectum and need not be recovered.

The capsule camera of the prior art allows the GI tract from the esophagus down to the end of the small intestine to be imaged in its entirety, although it is not optimized to detect anomalies in the stomach. Color photographic images are captured so that anomalies to be detected need only have small visually recognizable characteristics, not topography. The procedure is substantially pain-free and requires no anesthesia. The risk associated with the capsule passing through the body is minimal—certainly, the risk of perforation is much reduced relative to traditional endoscopy. The cost of the procedure is less than for traditional endoscopy due to the decreased use of clinician time and clinic facilities, and without using anesthesia.

In the prior art, a wireless capsule camera stores a single data stream.

SUMMARY OF THE INVENTION

According to one embodiment of the present invention, a capsule camera includes a wireless transmitter that transmits data and a receiving system having multiple receiving units to allowing storing multiple data streams simultaneously. The multiple stored data streams may be used at a later time to derive the best data stream for analysis, based on the network conditions at the time each data packet is received.

In general, wireless transmission is error prone. Bit errors in codeword may have a greater impact than the same number of bit errors in the image data. For example, a bit error located in a codeword or a header of a data packet is likely to be of greater consequence than a bit error located in the encoded data portion representing an image pixel value. Therefore, it is possible that a receiver under better network condition actually receives an encoded string that is more difficult to decode than another receiver under an inferior network condition. Due to noise in the environment and multi-paths, sometime a signal with an error may be received despite strong received signal strength. For the above and other reasons of secured wireless transmission, it is desirable to keep multiple received data streams in the receiving units.

The best data stream may be derived from the multiple stored data streams at a later time during the decoding process. For example, in a capsule camera application, the multiple data streams may be stored in the memory devices associated with the receiving units, which are typically attached to different locations on the body during diagnosis. The multiple data streams are maintained as the capsule passes through the gastrointestinal tract. Subsequently, after the diagnosis, the receiving units are recovered and connected to a computer or another standalone device for analysis. At that time, the best data stream is derived from the stored data streams using a decoding process, or by comparing the decoded results.

To improve efficiency, not all receiving units store the data streams at the same time. A screening process, for example, may be provided such that only the receiving units with better network conditions store the data streams. In a real-time system, the data streams may be stored for only a short duration before the best data stream is derived by a decoding process, or by comparing the decoded results.

The present invention is better understood upon consideration of the detailed description below in conjunction with the accompanying drawings.

DETAILED DESCRIPTION OF THE INVENTION

Figure 1:
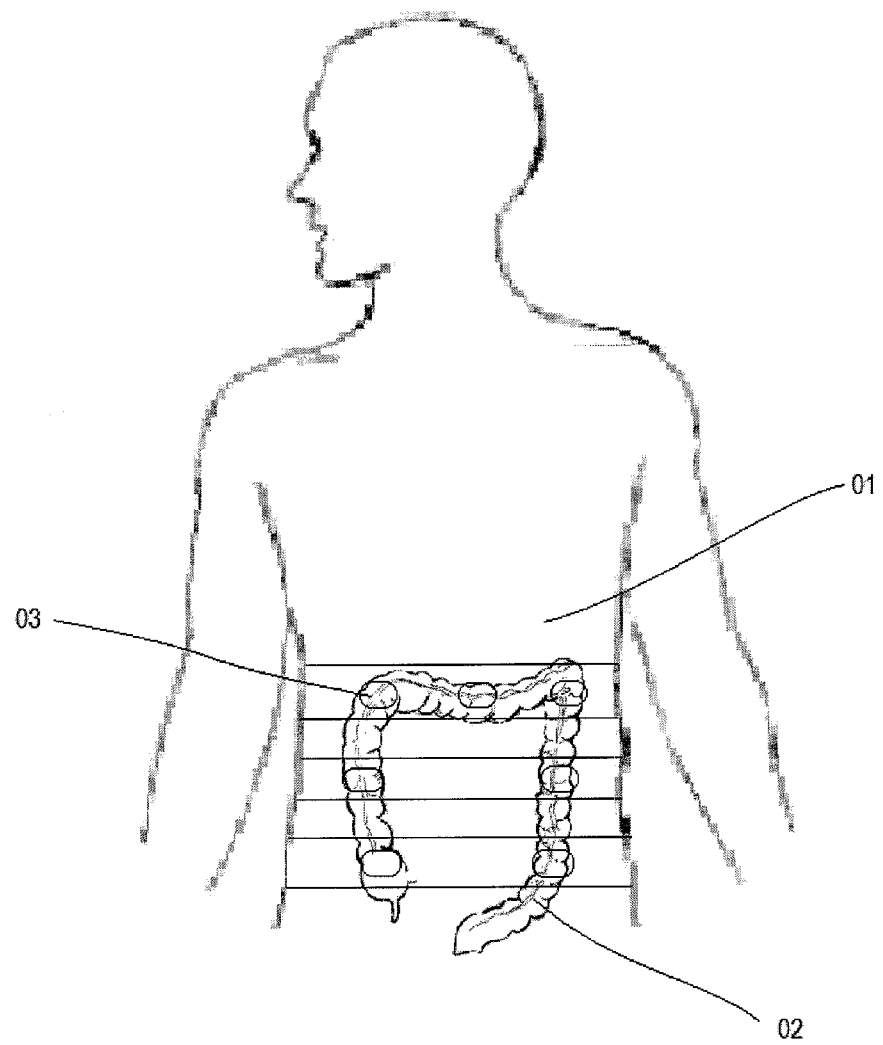
FIG. 1 shows, according to one embodiment of the present invention, receiving units 03 (each including a wireless receiver) being attached to human body 01.

A capsule camera that is equipped with a wireless transmitter is activated for image data and other data transmissions as it travels in a gastrointestinal tract. FIG. 1 shows, according to one embodiment of the present invention, receiving units 03 (each including a wireless receiver) being attached to human body 01. As shown in FIG. 1, receiving units 03 are placed at various locations over intestine 02, which is under examination, to receive image and other data from a capsule camera that is traveling in the gastrointestinal tract. Although FIG. 1 shows seven receiving units, any suitable number of receiving units may be used. The number of receiving units is determined based on system design considerations, such as human body transmission and receiving error rates. Each of receiving units 03 may be affixed to an assigned location of the body by belt, band or tape.

Figure 2A:
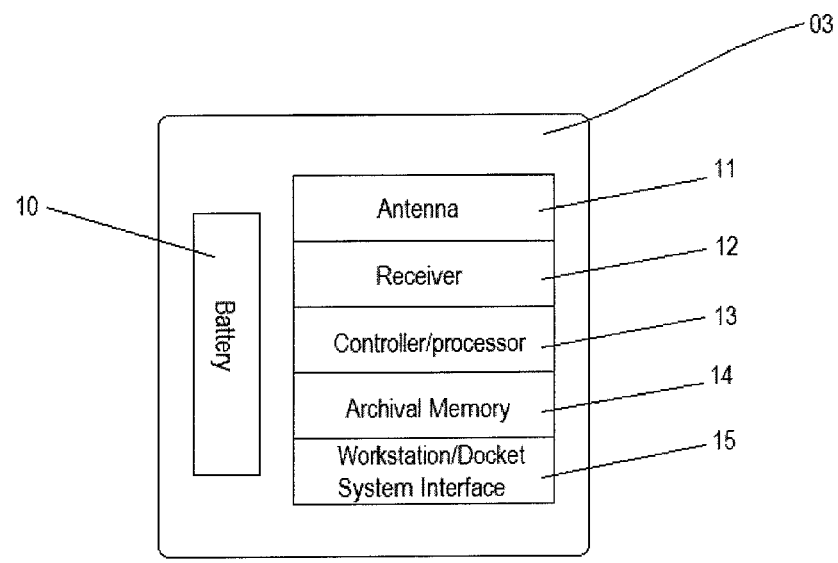
FIG. 2A is a block diagram of exemplary receiving unit 03, in accordance with one embodiment of the present invention.

FIG. 2A is a block diagram of an exemplary receiving unit 03, in accordance to one embodiment of the present invention. As shown in FIG. 2A, antenna 11 is provided for picking up a wireless signal. The captured signal is provided to receiver 12 to recover the transmitted data. The transmitted data includes both image data and other data. Such other data includes, for example, the time at which each data block is received and the network condition at the time the data block is received. The received data is stored in archival memory 14, which may be provided by a mini disk drive or a semiconductor memory device (e.g., a non-volatile memory device). At a later time, the data in receiving unit 03 may be retrieved through workstation/docket system interface 15 into an intermediate docketing system or directly into a workstation. Workstation/docket system interface 15 may be provided by a serial interface (e.g., USB) or a parallel port (e.g. PCMCIA). Controller/processor 13 controls receiving unit 03's operations and may handle other suitable functions, if required. This signal flow is represented in the flow diagram of FIG. 3. Battery 10, which may be provided by one or more battery cells, powers receiving unit 03.

Figure 2B:
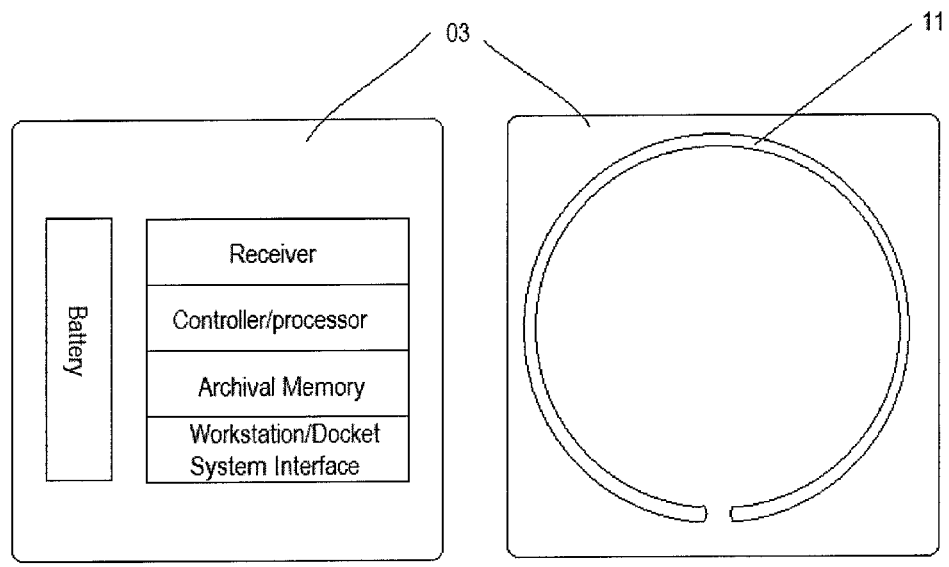
FIG. 2B shows, in one exemplary implementation, antenna 11 being located on one side of receiving unit 03, while other components of receiving unit 03 are located on the other side.

FIG. 2B shows, in one exemplary implementation, antenna 11 being located on one side of receiving unit 03, while other components of receiving unit 03 are located on the other side. Preferably, the antenna side of receiving unit 03 is provided on the side facing the human body to avoid the transmitted signal from being shielded by the other components of receiver unit 03.

Figure 3:
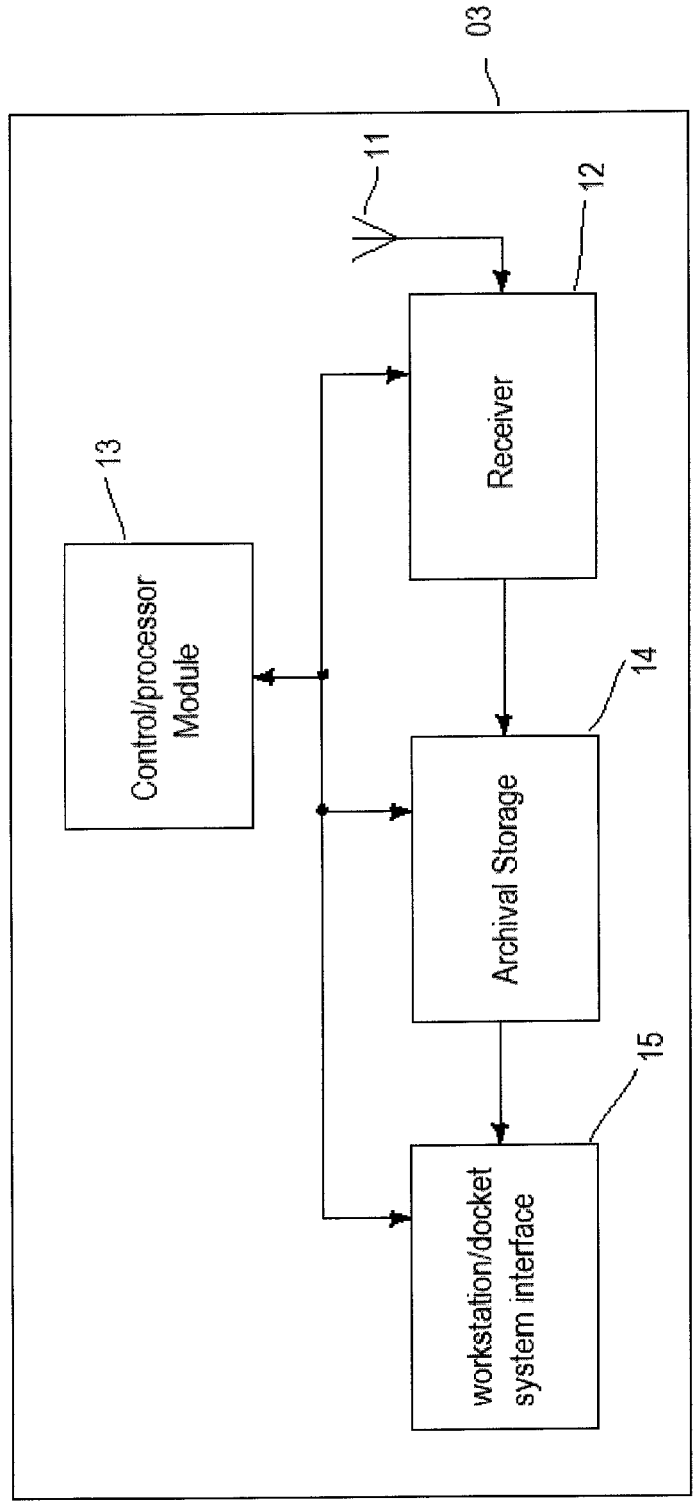
FIG. 3 is a signal flow diagram of receiving unit 03, in accordance with one embodiment of the present invention.
Figure 4A:
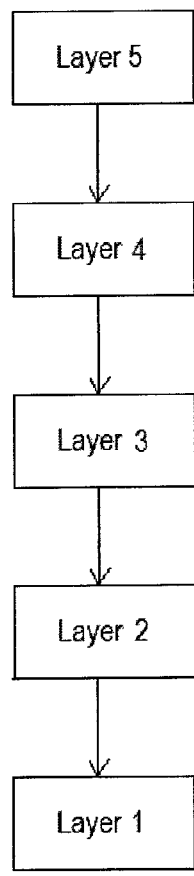
FIG. 4A shows the protocol stacks in a capsule camera and a receiving unit, in accordance with one embodiment of the present invention, in accordance with one embodiment of the present invention.
Figure 4A:
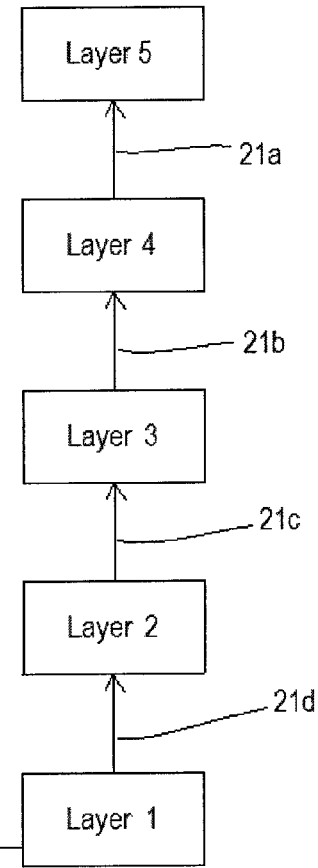
Figure 4B:
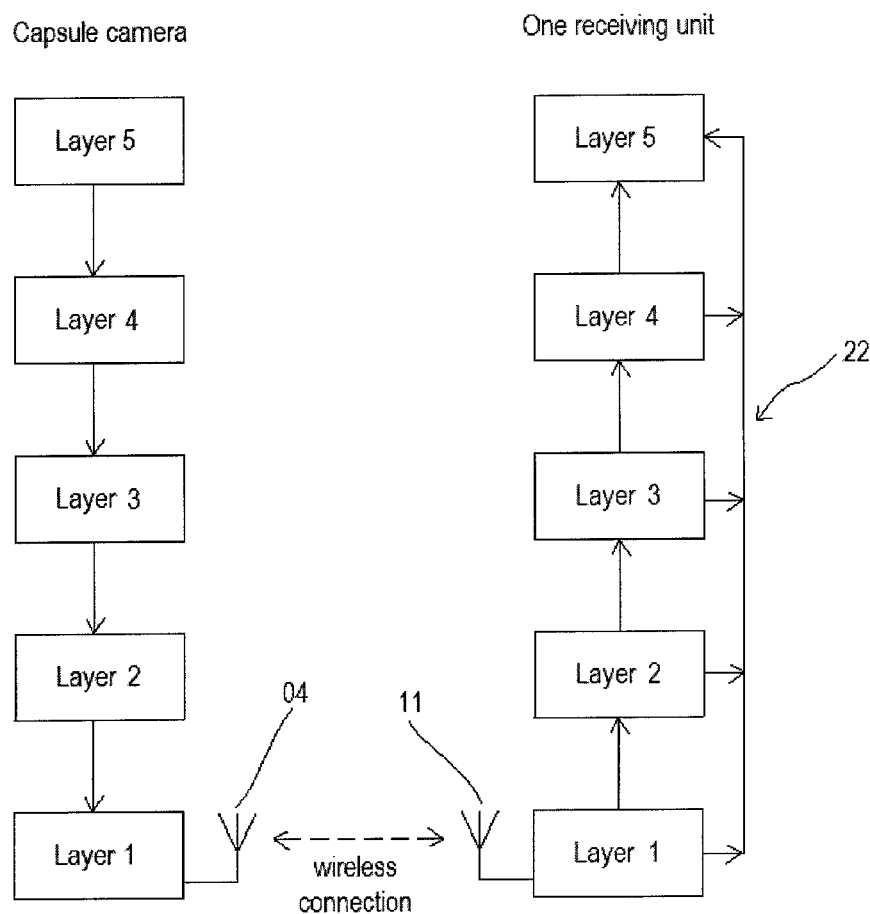
FIG. 4B shows passing network condition information to the top protocol layer of receiver 12 on separately provided path 22 without going through the strict hierarchical layer convention.

FIG. 4A shows the protocol stacks in a capsule camera and a receiving unit, in accordance with one embodiment of the present invention. As shown in FIG. 4A, five communication protocol layers 1-5 are provided in both the capsule camera and the receiving unit, each protocol layer in the capsule camera having a peer protocol layer in the receiving unit. Of course, other implementations are possible. The physical layers communicate over a wireless medium between transmission antenna 04 of the capsule camera and receiving antenna 11 of the receiving unit. The wireless medium includes the human body and possibly an air gap. The protocol decoder resides in receiver 12 (FIG. 3). Network condition information is passed from layer to layer (i.e., 21d, 21c, 21b to 21a, in that order) to the top protocol layer of the receiver 12, and retrieved by controller/processor 13 to be stored in archival memory 14. Each of interfaces 21a-21d has access to network condition information of all the layers beneath it. FIG. 4B shows passing network condition information to the top protocol layer of receiver 12 on separately provided path 22 without going through the strict hierarchical layer convention. This is convenient, as error conditions in each layer cannot be anticipated by the peer protocol layers in the capsule camera.

In one system, a capsule camera traveling through the GI tract is tracked by a number (e.g., M) of receiving units, with each receiving unit being provided to record one data stream and one set of network conditions. At each receiving unit, the data stream may have gaps due to unfavorable network conditions during certain time periods. For example, suppose the probability of successfully transmitting a K-bit block of data is S (naturally, S≤1.0). Under the same network condition, the probability for successfully transmitting a 2K-bit block would be $S^2$. Thus, for a large enough K, the probability of error-free transmission may be impractically low. This consideration is particularly relevant, as the capsule camera is moving through the body during this time, so that the capsule camera may pass through a section of the GI tract where the K-bit block is optimal into another section of the GI tract where a K-bit block may be too large and thus the associated transmission time is too long. Because the network conditions along the GI tract may vary and the speeds at which the capsule camera moves in the GI tract may also vary along the GI tract, the value K of the optimal block size at any given time depends in general on both the locations of the capsule camera in the GI tract and the associated receiving unit.

Some encoding algorithms must operate within a defined encoding/decoding data unit (e.g., an image area between restart markers, a slice or a group of frames). An error in one data unit is not propagated to the next data unit. Thus, in one embodiment, the optimal block size depends also on locations of the boundaries between encoding/decoding data units.

If the receiving units are placed at multiple locations (e.g., the locations shown in FIG. 1), each receiving unit must keep track of time, so that the individually stored received data blocks of these receiving units may be correlated to allow assembling into a single data stream at a subsequent time for viewing or processing. The single data stream may be derived in a dedicated system, a docket system, or a workstation. The clock signals in the receiving units must be synchronized with respect to each other at the beginning of data collection to accuracy (expressed in ppm) within a predetermined value. That is, synchronization must take place at the start or not long before the start of data collection (e.g., at the time the receiving units are placed on the patient's body) by a docket system or by a workstation. In one embodiment, synchronization is performed by resetting all receiving units simultaneously or by synchronizing two or more receiving units at a time, until all receiving units are synchronized with respect to each other. If the transmission time for a block is $T_S$, then each receiving unit clock must be kept accurate to an error of less than $T_S/2$ over the entire duration of diagnosis. Alternatively, timing information may be transmitted by the capsule camera along with the image or other data to mark the time at which the image or other data is collected. The frequency at which such timing information must be transmitted is such that, in general, the greatest time difference between any two receiving units is less than $T_S/2$. In this way, it is not necessary to synchronize the time of receiving units at the beginning and use a precision crystal oscillator to keep accurate time: an on-chip semiconductor clock circuit may be sufficient.

Figure 5A:
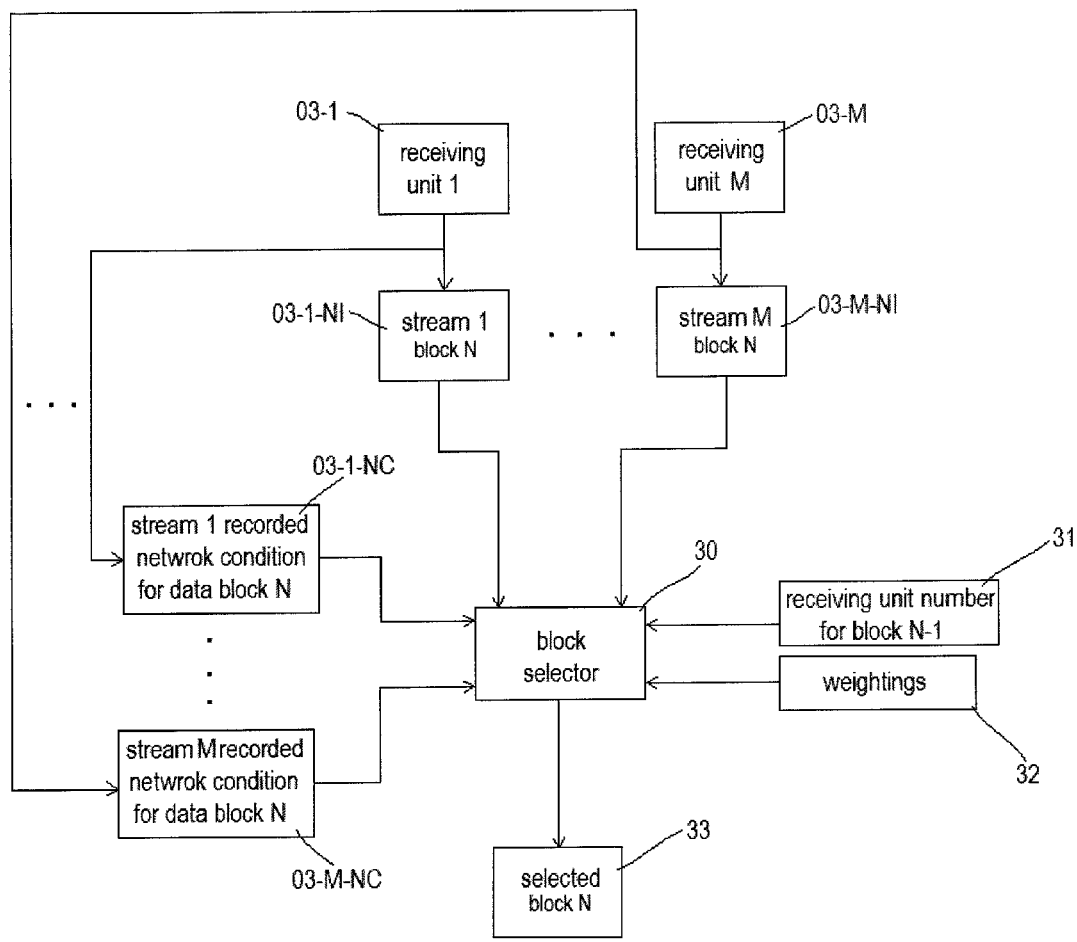
FIG. 5A shows a process for selecting an optimal block N, during time period $T_N$, from the data streams recorded in the receiving units, in accordance with one embodiment of the present invention.

FIG. 5A shows a process for selecting, during time period $T_N$, an optimal block N from the data streams recorded in the receiving units, in accordance with one embodiment of the present invention. Such a selection process may be executed after diagnosis is complete, and after the receiving units are detached from the human body and are connected to the docket system or workstation (e.g., such as a personal computer). A personal computer typically does not have sufficient input ports (e.g., USB ports) for connecting all the receiver units simultaneously. In that situation, a hub (e.g., a USB hub) may be used. The selecting process of FIG. 5A may be executed on the workstation. As shown in FIG. 5A, to select the Nth block, block selector 30 selects one block from M blocks (i.e., block 03-1-NI to block 03-M-NI), corresponding to the M data streams stored in the M receiving units 03-1 to 03-M, respectively. The selected block 33, is selected based on the network conditions 03-1-NC to 03-M-NC, which are stored along with the image data in the M receiving units, respectively. There may be gaps in general in the data stream of each receiving unit. If no Nth data block—corresponding to time period $T_N$—is found in a particular receiving unit, block selector 30 does not take into account an Nth block from that receiving unit.

If block selector 30 has determined that the best (N−1)th block came from a certain receiving unit data stream, then the receiving unit is also favored in the Nth block selection (see reference numeral 31 in FIG. 5A). Weighting factor 32 may be provided to block selector 30, with the weighting function being determined empirically. The process memory may reach back to any number of blocks prior to the current Nth block, with each previous block being assigned a different weight, depending on the time difference between the previous block and the current Nth block.

Figure 5B:
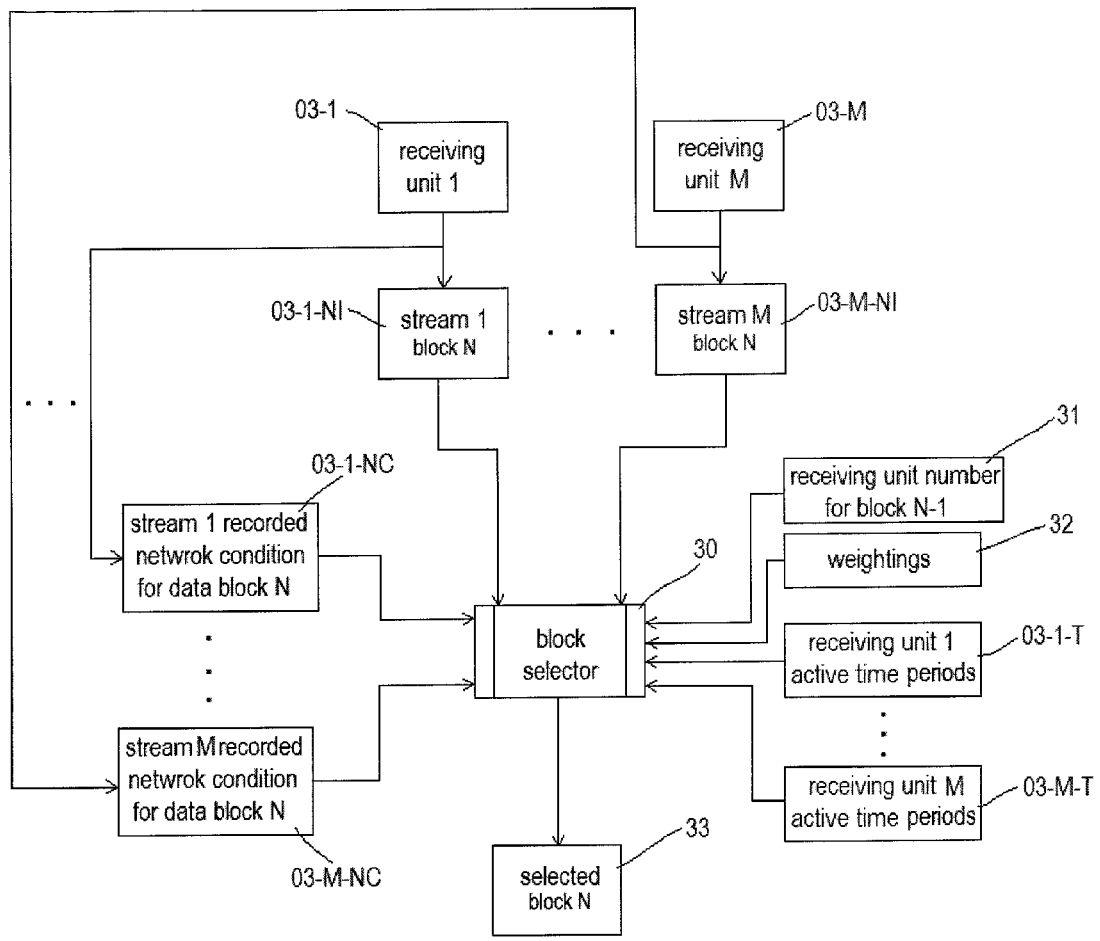
FIG. 5B shows a selecting process in which the active time periods for each receiver (labeled 03-1-T to 03-M-T, respectively) are provided as inputs to block selector 30, in accordance with one embodiment of the present invention.

As described below, during the course of diagnosis, a receiving unit may be placed in a power-saving mode (e.g., turned off or put into a sleep mode). These inactive time periods may be predetermined time points or be determined based on the progress of the diagnosis process and may be recorded in the receiving units as either active time periods or inactive time periods. FIG. 5B shows a selecting process in which the active time periods for each receiver (labeled 03-1-T to 03-M-T, respectively) are provided as inputs to block selector 30. Block selector 30 does not take into account any block transmitted during a period of time that is specified as an inactive time period for a receiving unit.

Figure 6:
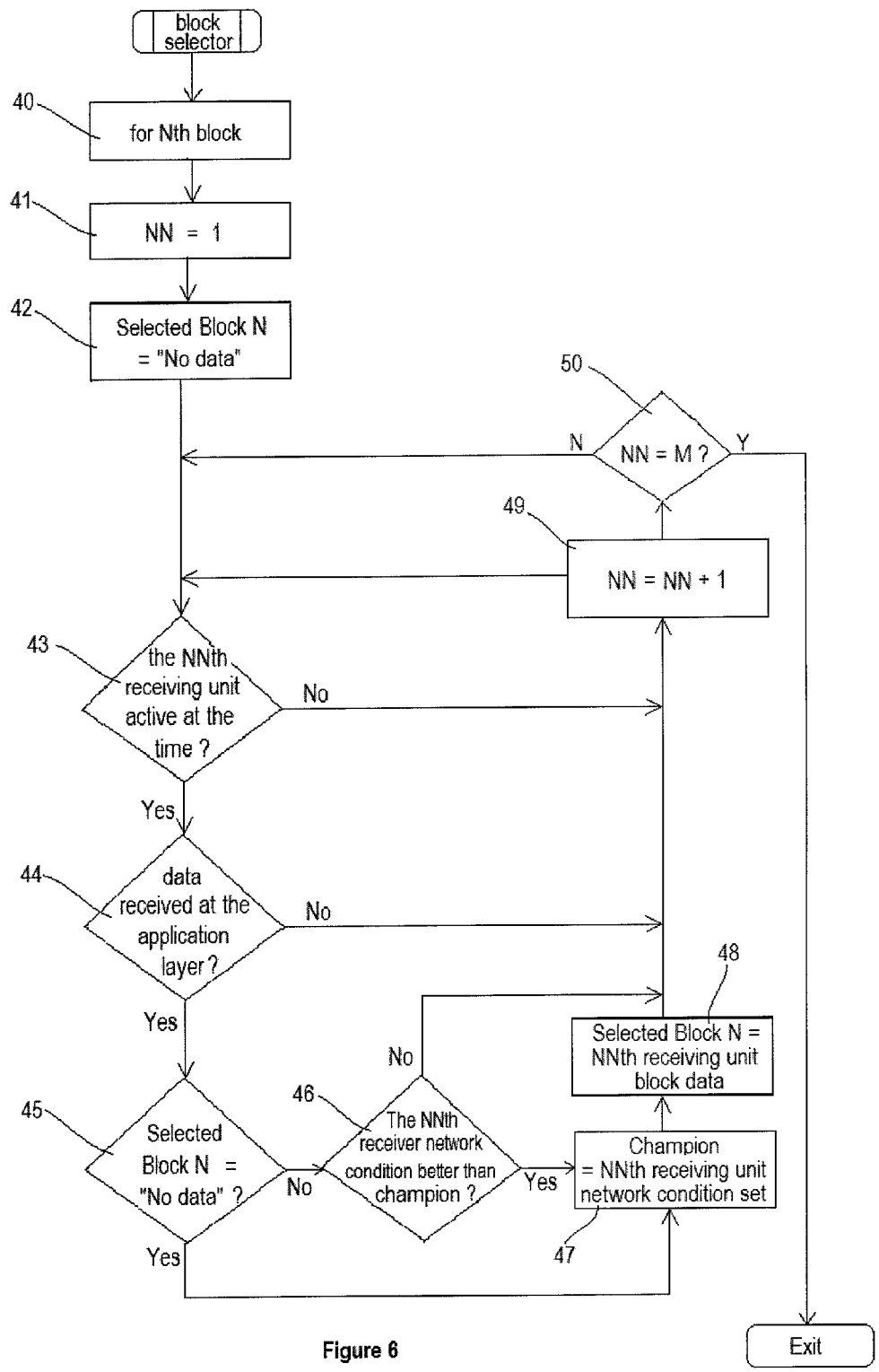
FIG. 6 is a flow chart for selecting the Nth block in one implementation of block selector 30 of FIG. 5B.

FIG. 6 is a flow chart for selecting the Nth block in one implementation of block selector 30 of FIG. 5B. As shown in FIG. 6, step 41 initializes to '1' a current value for the running index of the receiving units. Step 42 initializes the selected block N to the label "no data," indicating that the candidate blocks have not been selected. When it is determined that the current receiving unit is active (step 43), selector 30 determines if data has been received into the application protocol layer (step 44). If the receiving unit is marked inactive, or if no data has been received into the application protocol layer, the current receiving unit is skipped. Initially, the first receiver that is active for the Nth block and which has received data into the application protocol layer is designated the "champion" with its associated network conditions (step 47) and selected as the selected Nth block (step 48). Thereafter, the network conditions of receiving units with active Nth blocks are compared one by one with the network condition of the champion (step 46). If the network condition of a given block compares favorable over the network condition of the champion, the given block is made the champion (step 47). Otherwise, the network condition of the next receiving unit is examined. The champion existing after the blocks of all the receiving units have been examined is the selected Nth block.

The network condition in the physical layer may be a combination of measured signal parameters (e.g., the peak-to-peak amplitude of the received signal, the frequency-phase lock condition, and the received signal strength indicator (RSSI) output of the received signal). For higher protocol layers, the error check and correction statistics may be used to indicate network condition. For example, error statistics that can be used include, for example, the type of errors, where the errors occur and the portion of errors that are correctable. Another indicator is the number of characters expected between data unit delimiters. For any given block (e.g., the Nth block), there are many ways for comparing network conditions between two receiving units.

Figure 7A:
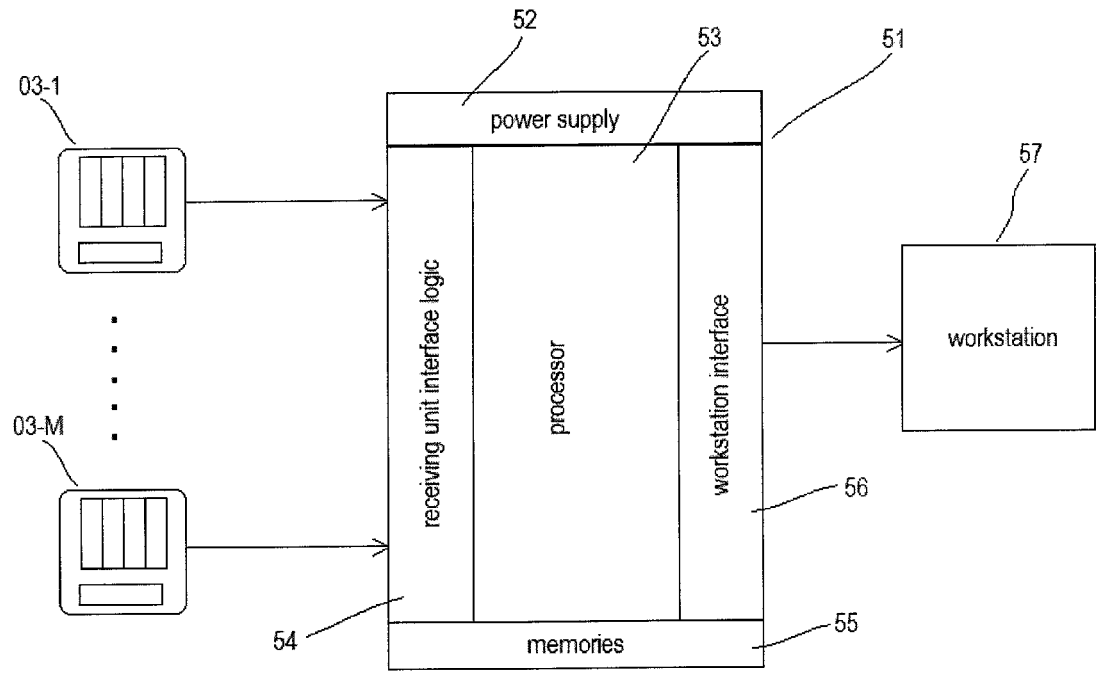
FIG. 7A shows the connections and data flow between receiving units 03-1 to 03-M and docket station 51 and between docket station 51 and workstation 57.

After the capsule camera has traveled through the intended GI tract 02 (i.e., after diagnosis is complete), receiving units, 03-1 to 03-M, are recovered from human body 01 and connected to docket system 51 or workstation 57 for further processing. FIG. 7A shows the connections and data flow between receiving units 03-1 to 03-M and docket station 51 and between docket station 51 and workstation 57, which may be a personal computer or another dedicated computational hardware. Docket system 51 may be provided with physical connection sockets for the receiving units (not shown), controlled by receiving unit interface logic 54, and processor 53. In addition, docket system 51 includes work station interface 56 and working memories 55. Processor 53 may be dedicated hardware, one or more processors, or a combination of processors and dedicated hardware. Docket system interface 56 connects to workstation 57, where the processed image data and other data are stored, analyzed, further processed or are sent to display. In one implementation, the block selecting processes described in conjunction with FIG. 5A or 5B may be implemented in docket system 51 or workstation 57.

Figure 7B:
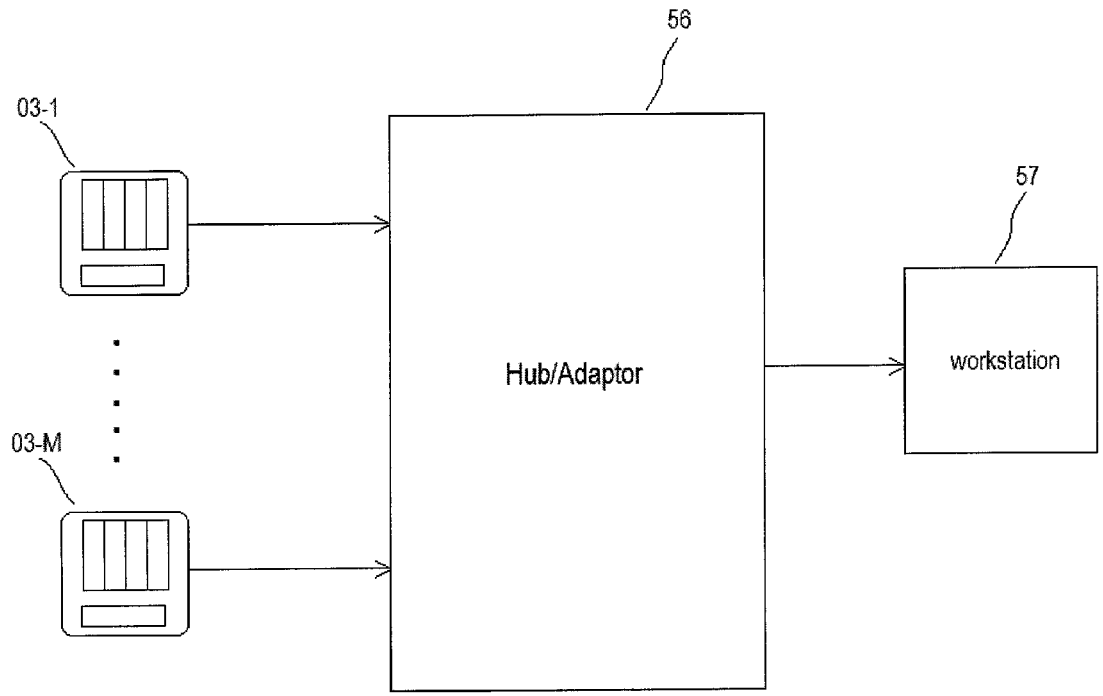
FIG. 7B shows an alternative implementation in which hub or adaptor 56 connects receiving unit 03-1 to 03-M to workstation 57.

FIG. 7B shows an alternative implementation in which hub or adaptor 56 connects receiving unit 03-1 to 03-M to workstation 57. In this implementation, one of the block selecting functions described above in conjunction with FIGS. 5A and 5B or FIG. 11A or 11B is implemented in the workstation 57. In FIGS. 7A and 7B, data flows from the receiving units (i.e., receiving units 03-1 to 03-M) to docket system 51 and to workstation 57, control signals may be bi-directional. In one implementation, power may be supplied to receiving units 03-1 to 03-M by docket system 51 or workstation 57. In one implementation, power to docket system 51 is supplied by workstation 57.

While FIG. 1 shows all receiving units (i.e., receiving units 03-1 to 03-M) to be active during diagnosis, the capsule camera in the GI tracts 02 is at a single location at any given time. By measuring a sufficiently large number of patients under similar medical conditions, it is possible to collect statistics on the required time for the capsule camera to reach any of a number of locations of interest in the GI tract. Using such statistics, at the time the capsule camera is expected to arrive at an area of interest, over or near which a receiving unit is positioned, the specific receiving unit may be activated, while the other receiving units may remain in an inactive mode. Alternatively, the specific receiving unit and its immediate neighbors may be activated. In one embodiment, a receiving unit may be placed to serve two areas of interest, based on the statistics of expected capsule passing times at the two locations.

Figure 8:
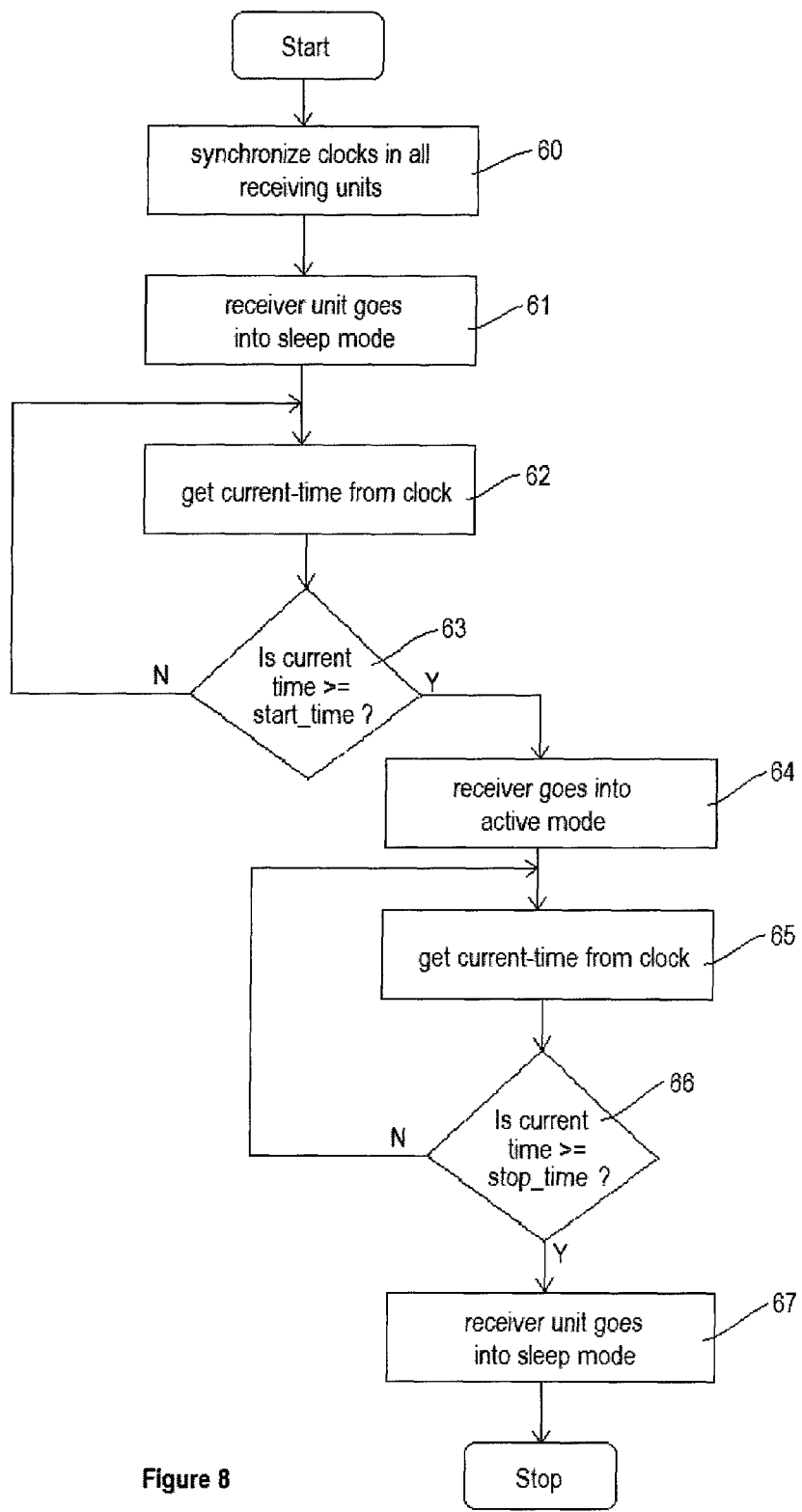
FIG. 8 is a flowchart that illustrates activating and deactivating one receiving unit 03, based on collected statistics that predict the location of a capsule camera.

FIG. 8 is a flowchart that illustrates activating and deactivating one receiving unit 03, based on collected statistics that predict the location of a capsule camera. After synchronizing all clock signals (step 60), the receiving unit goes into an inactive mode (61) and is activated when the current time reaches a start time at which the capsule camera is expected to arrive at the location of the receiving unit (steps 62-64). During the period the capsule camera is active, image and other data are collected and transmitted. The capsule camera returns to the inactive state when a stop time is reached (steps 65-67). The stop time is the expected time at which the capsule camera passes out of the area of interest relevant to the receiving unit. To ensure that image data of the area of interest is properly captured, nearby receiving units may be activated, even when these nearby receiving units are placed outside of the zone within which the capsule camera is likely to be.

Figure 9:
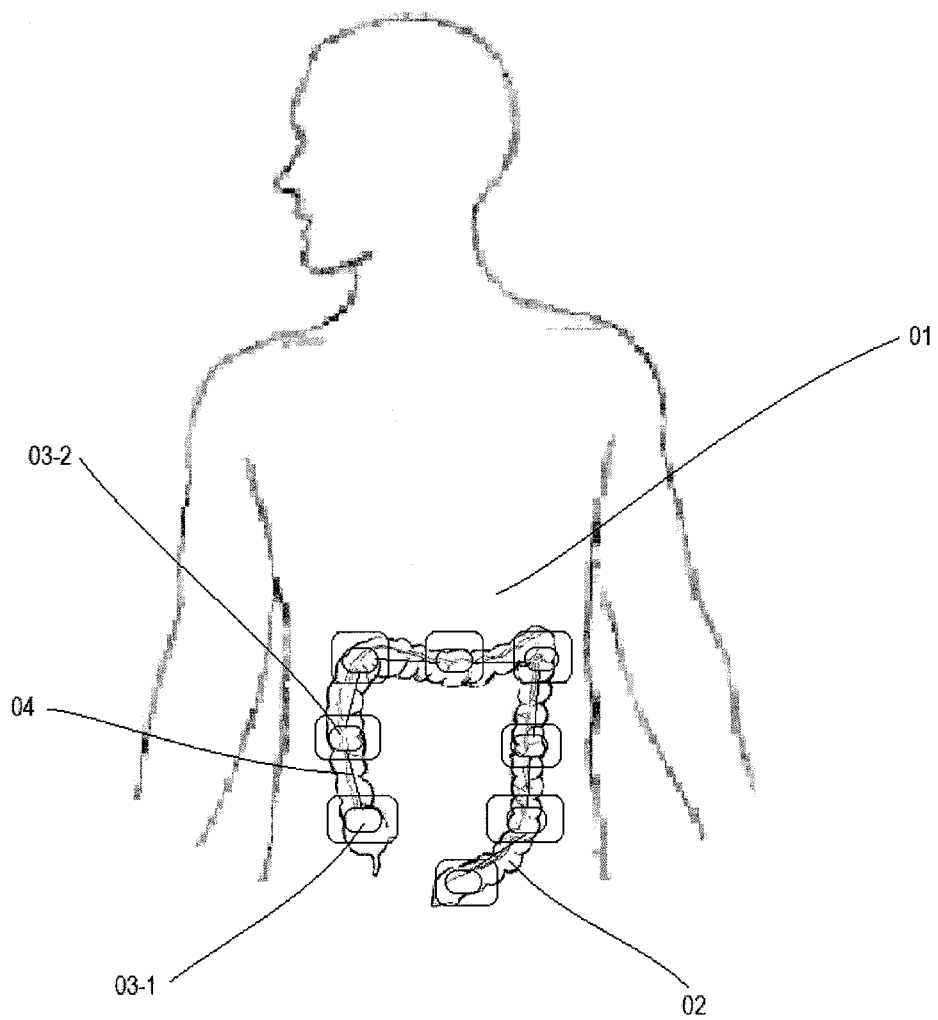
FIG. 9 shows receiving units 03-1, 03-2 and other receiving units being placed on human body 01.

FIG. 9 shows receiving units 03-1, 03-2 and other receiving units being placed on human body 01. Receiving units 03-1, 03-2 and others may be connected by bus 04, for example. Bus 04 may be used to carry data, control signals, timing information, clock signals and power supply. The receiving units of FIG. 9 may be connected by wired or wireless links. In one embodiment, receiving units 03 may communicate with each other or at least with neighboring receiving units.

Figure 10:
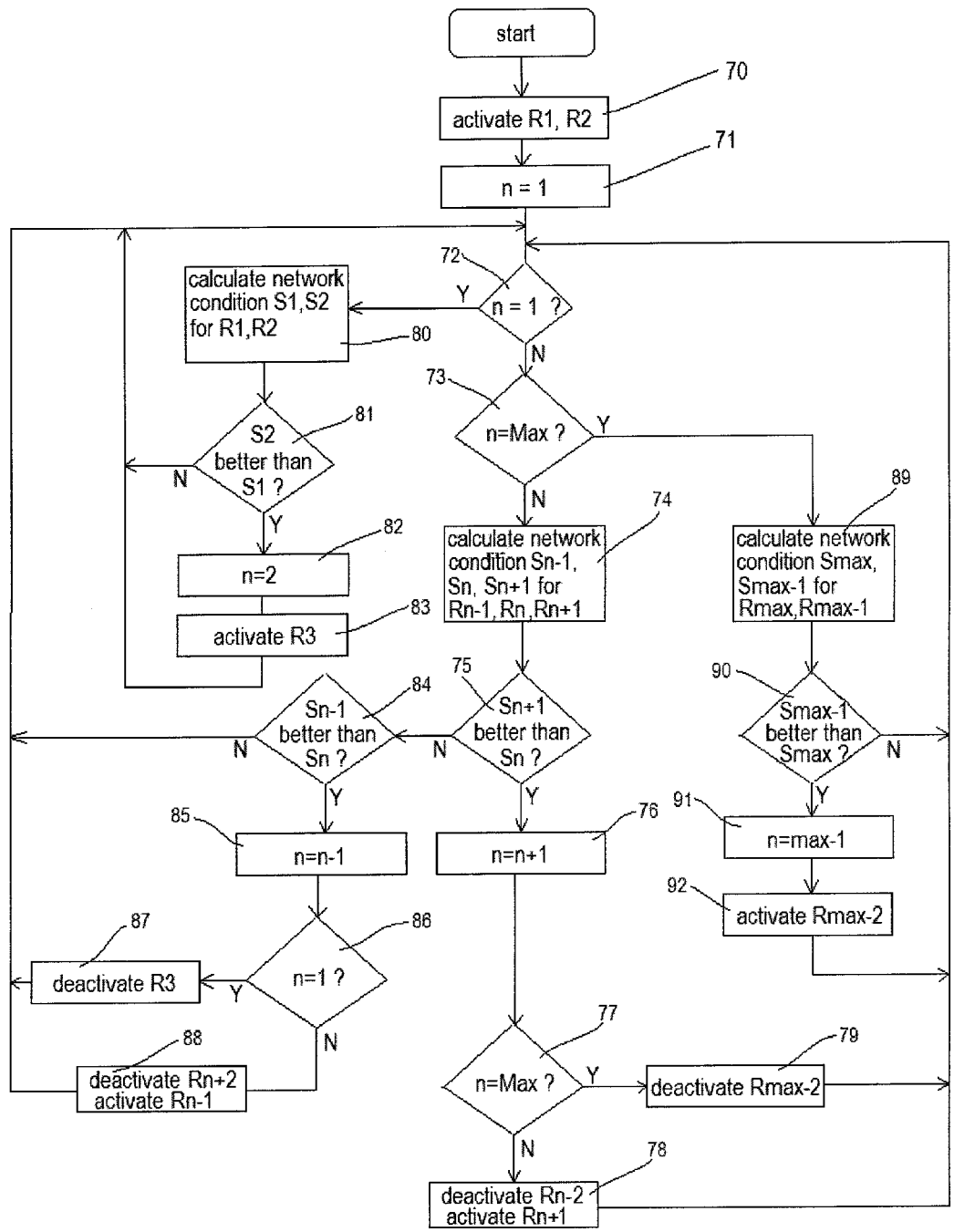
FIG. 10 shows an activation scheme for activating consecutively numbered receiving units, according to one embodiment of the present invention.

FIG. 10 shows an activation scheme for activating consecutively numbered receiving units, according to one embodiment of the present invention. As shown in FIG. 10, receiving units 03 are consecutively numbered from 03-1 to 03-M and placed in numerical order along GI tract 02 in the mouth to anus direction. For example, to examine the entire colon, receiving unit 03-1 may be placed over the colon closest to ileocecal valve. Once the capsule camera (not shown) arrives at the small intestine-colon interface (i.e., the ileocecal valve), first receiving unit 03-1 is readily activated and ready for receiving data transmitted from the capsule camera. In FIG. 10, to ensure signal capture, receiving unit 03-2 is also activated (steps 70-71). Under the activation scheme of FIG. 10, the network conditions at the activated receiving units are used to select which one of the activated receiving units is the current receiving unit. When the network condition S2 detected at receiving unit 03-2 is more favorable than the network condition S1 detected at receiver 03-1, the current receiving unit is set to receiving unit 03-2, and receiving unit 03-3 is activated (steps 72, 80-83). As the capsule camera moves to a position next to receiving unit 03-NM, the activation scheme makes receiving unit 03-NM the current receiving unit, while having, at the same time, receiving units 03-(NM−1) and 03-(NM+1) activated (steps 72-78). Receiving unit 03-(NM−2) is deactivated when receiving unit 03-(NM+1) is activated (step 78).

From time to time, the capsule camera may retrograde, so that the network condition S(NM−1) at receiving unit 03-(NM−1) may actually become more favorable than network condition 03-(NM) at receiving unit 03-(NM). When that situation arises, the current receiving unit is reset to 03-(NM−1) (steps 72-75, 84-85). In the activation scheme of FIG. 10, the activated receiving units are the current unit and one receiving unit in each of the forward and backward directions. In general, it is not necessary to have equal number of activated receiving units in the forward and backward directions. For example, we may have d+ receiving units in the forward direction and d− receiving units in the backward direction. For NM=5, with d+=2 and d−=1, the activated receiving units are receiving units 03-5, 03-6, 03-7 and 03-4. Furthermore, at different sections of the GI tract, as motility may be different, having different d+ and d− values may be appropriate. In one embodiment, when comparing network conditions (e.g., at decision points 75, 81, 84 and 90), the current receiving unit may be assigned a more favorable weighting factor. Steps 89-92 handle the last receiving unit 03-M, when receiving units 03-M and 03-(M−1) are activated.

The activation schemes provided in FIG. 8 (i.e., according to expected transit times) and FIG. 10 (i.e., according to received signal strengths) may simplify the calculations required in the block selecting processes illustrated in FIGS. 5A and 5B. These activation schemes may also simplify the decoding selecting process of FIGS. 11A and 11B discussed below. The activation schemes may also save power and storage area, may reduce the reception and storage of erroneous data, and may reduce the electromagnetic interference (EMI) of the total system operation. In the block selecting processes of FIGS. 5A and 5B, one block is selected based on network condition. However, different bit errors have different impact on the affected block or data stream. A bit error in a codeword may cause, for example, the codeword to become a codeword with a different run length. Such an error has a greater impact during decoding than a bit error in a pixel value. Although an error resilient coding/decoding may be applied, such a procedure incurs a penalty on the compression ratio, complexity and power, which are all critical considerations in capsule camera design (in fact, on all handheld wireless devices, in general). Even with an error resilient coding/decoding, error-free operation is not guaranteed. So the decoding process itself is the best selection mechanism, if the block selection processes of FIGS. 5A and 5B may result one or more best candidates for each block.

Figure 11A:
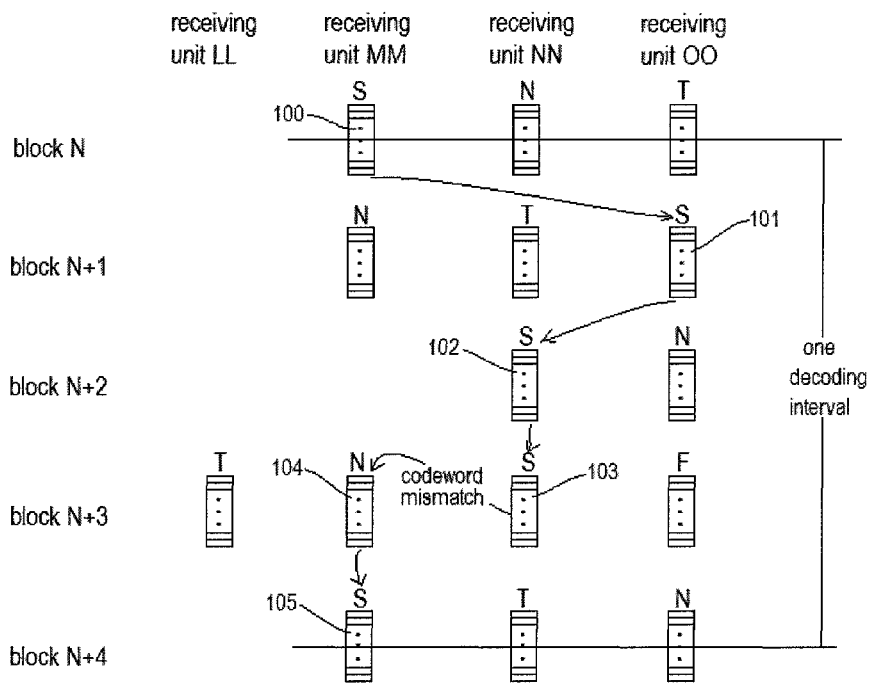
FIG. 11A show a decoding process which provides a stream of blocks based on network conditions and decoding criteria, in accordance with one embodiment of the present invention.
Figure 11B:
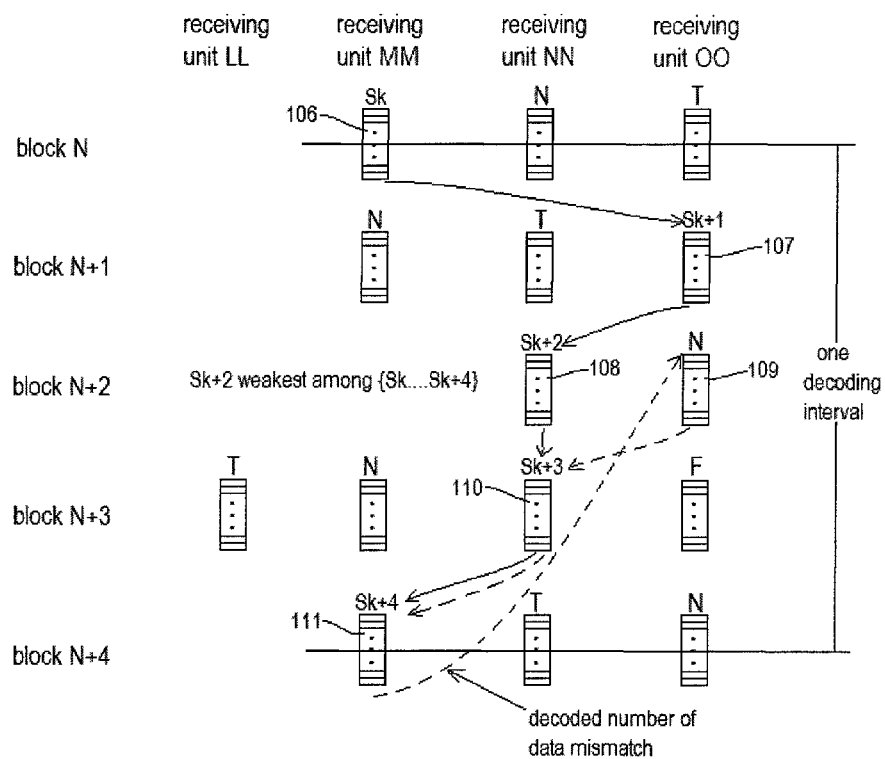
FIG. 11B show a decoding process which provides a stream of blocks based on network conditions and decoding criteria, in accordance with another embodiment of the present invention.

FIG. 11A show a decoding process which provides a stream of blocks based on network conditions and decoding criteria, in accordance with one embodiment of the present invention. In FIG. 11A, consecutive block sequences N to N+4 include a decoding interval (i.e., a data unit for decoding). In this embodiment, the best stream of blocks are selected from blocks received into different receiving units (i.e., receiving units LL, MM, NN and OO) at different block sequences according to network conditions. At block sequence N, for example, block 100—which is received into receiving unit MM—is selected because it is associated with the strongest network condition. (It is preferred that the decoding interval coincides with block boundaries, but the teachings of FIGS. 11A and 11B are applicable to more general conditions). At block sequence N+1, the decoding process of FIG. 11A selects block 101, which is associated with the strongest network condition detected at receiving unit OO. At block sequence N+2, the block selector provides blocks from only two receiving units. Thus, the decoding process selects block 102, which is associated with the better network condition between receiving units NN and OO. At block sequence N+3, the decoding process encounters a decoding error while decoding block 103, which is associated with the strongest network condition among receiving units LL, MM, NN and OO. Therefore, the decoding process selects block 104, which is associated with the next best network condition (i.e., at receiving unit MM). Decoding restarts from where block 102 left off, so that the decoding process concatenates the decoded bits from blocks 102 and 104. The decoding process then selects block 105, which is associated with the strongest network condition at block sequence N+4. The best data stream is therefore the decoded bits resulting from decoding the concatenated bits within decoding interval from block 101, block 102, block 104, and block 105.

FIG. 11B show a decoding process which provides a stream of blocks based on network conditions and decoding criteria, in accordance with another embodiment of the present invention. In FIG. 11B, as in FIG. 11A, consecutive block sequences N to N+4 include a decoding interval. In addition, in FIG. 11B, Sk, Sk+1, Sk+2, Sk+3, and Sk+4 denote the strongest network condition for block sequence N, N+1, N+2, N+3, N+4, respectively. As shown in FIG. 11B, as the decoding process proceeds from block sequence N to block sequence N+4, blocks 106, 107, 108, 110 and 111 are selected according to the network condition at each block sequence. However, while processing block 111, it is found that the total number of characters in the decoding interval do not match the expected number of characters in the decoding interval. To correct this error, since block 108 is associated with the weakest network condition among the network conditions associated with blocks 106, 107, 108, 110 and 111, the decoding process of FIG. 11B discards block 108, and selects instead block 109. Decoding completes using blocks 106, 107, 109, 110 and 111. In general, the decoding error may be detected at an earlier time than at the end of the decoding interval (i.e., in block 111). For those skilled in the art, suitable corrections during the decoding process would be apparent from the examples provided in FIGS. 11A and 11B, and their variations and modifications.

Although FIGS. 11A and 11B provide illustrative examples for compressed bit streams, using the decoding process to select the best streams of blocks is applicable to any encoded data streams. The errors in delimiters or with inconsistent character lengths are more serious than other bit errors. Thus, the decoding process is effective in selecting the best stream of blocks. In other embodiments, the decoding process need not complete to allow effective block selection. For example, it is already beneficial if the decoding process merely checks the bit stream header information, syntax, character lengths and other errors but does not actual perform decoding during selection of the best stream of blocks. In other embodiments, the decoding, partial decoding, and error detection processes may be carried out in the block selector, such as that shown in conjunction with FIGS. 5A and 5B.

Block selections using the decoding process, such as illustrated by FIGS. 11A and 11B, may be implemented in docket system 51, workstation 57 or both, to allow sharing of the computation load. If docket system 51 and workstation 57 share the computation load, the data flow between docket system 51 and workstation 57 in FIG. 7A may be bi-directional for the intermediate data. In one embodiment, the processing power in the receiving units of FIGS. 7A and 7B may also be used as coprocessors. Thus, receiving units 03-1 to 03-M, docket system 51 and workstation 57 may form a distributed computing system.

To reduce the processing time required to derive the best data stream out of multiple data streams, the selection process, such as illustrated by the processes discussed in conjunction with FIGS. 11A and 11B, may be carried out in the receiving units. While the receiving units are storing received incoming streams, the processor in each receiving unit may perform the tasks discussed in conjunction with FIGS. 5a, 5b, 11A and 11B. In one embodiment, such processing may be carried out during times when the processor can spare processing power and when the receiving unit is supposed to be inactive, i.e. not receiving signals. In another embodiment, multiple processor units are provided in controller/processor modules of FIGS. 2 and 3. In one embodiment, the processes are carried out according to a schedule that is based on the power reserve on the battery of the receiving units, the elapsed time since the capsule has been activated, and the received data.

Figure 12A:
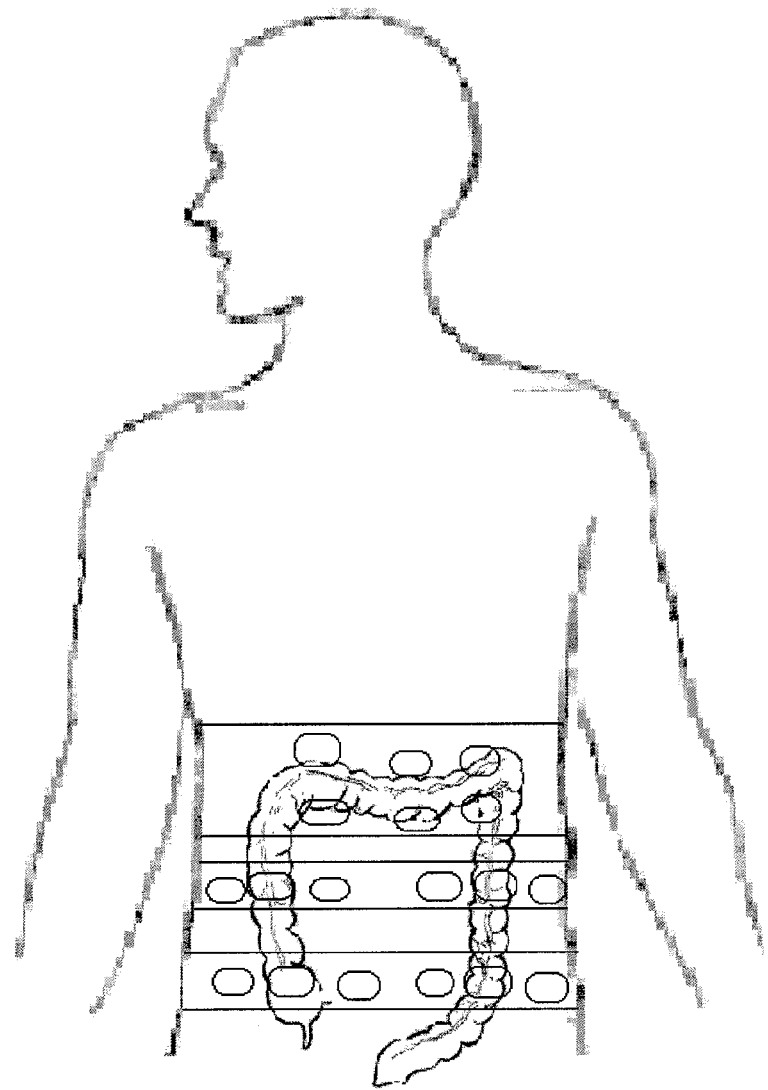
FIGS. 12A to 12E illustrate various placements of receiving units on a patient's body, in accordance with various embodiments of the present invention.
Figure 12B:
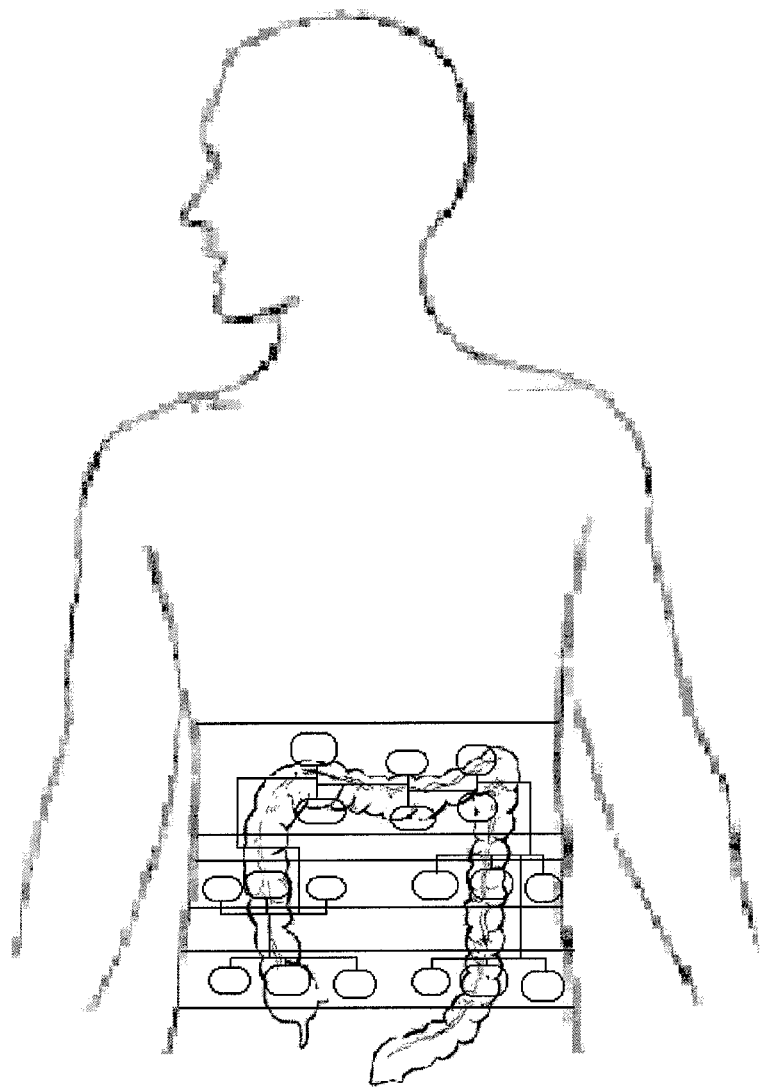
Figure 12C:
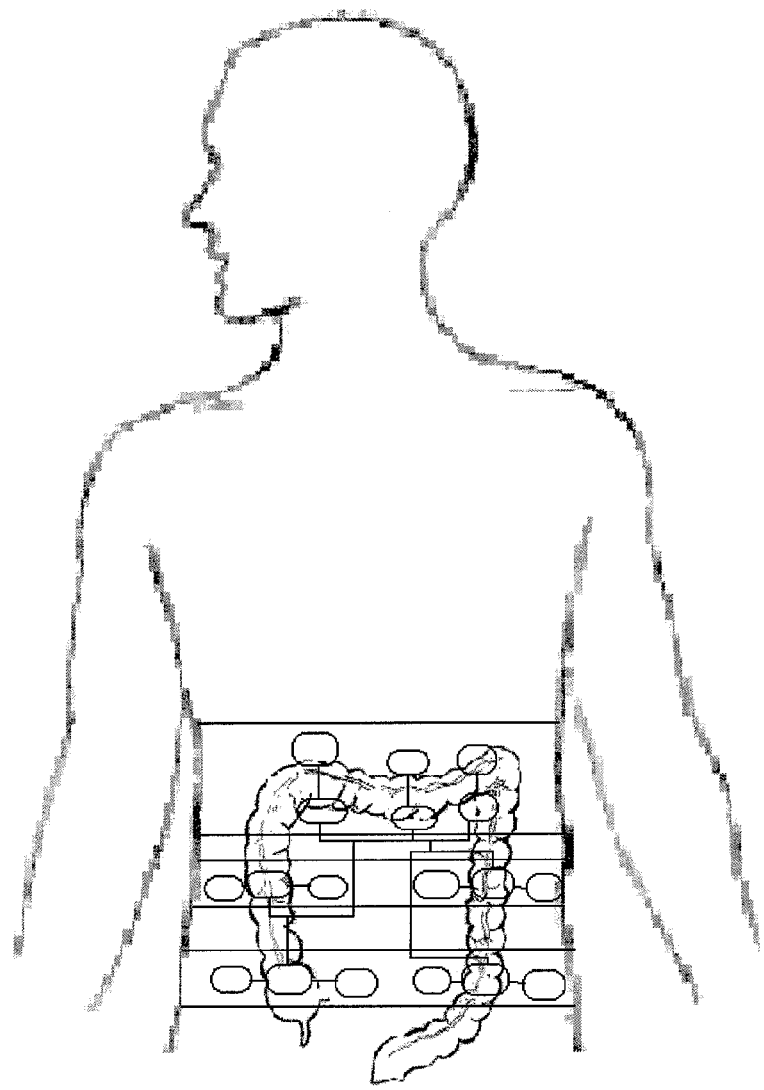
Figure 12D:
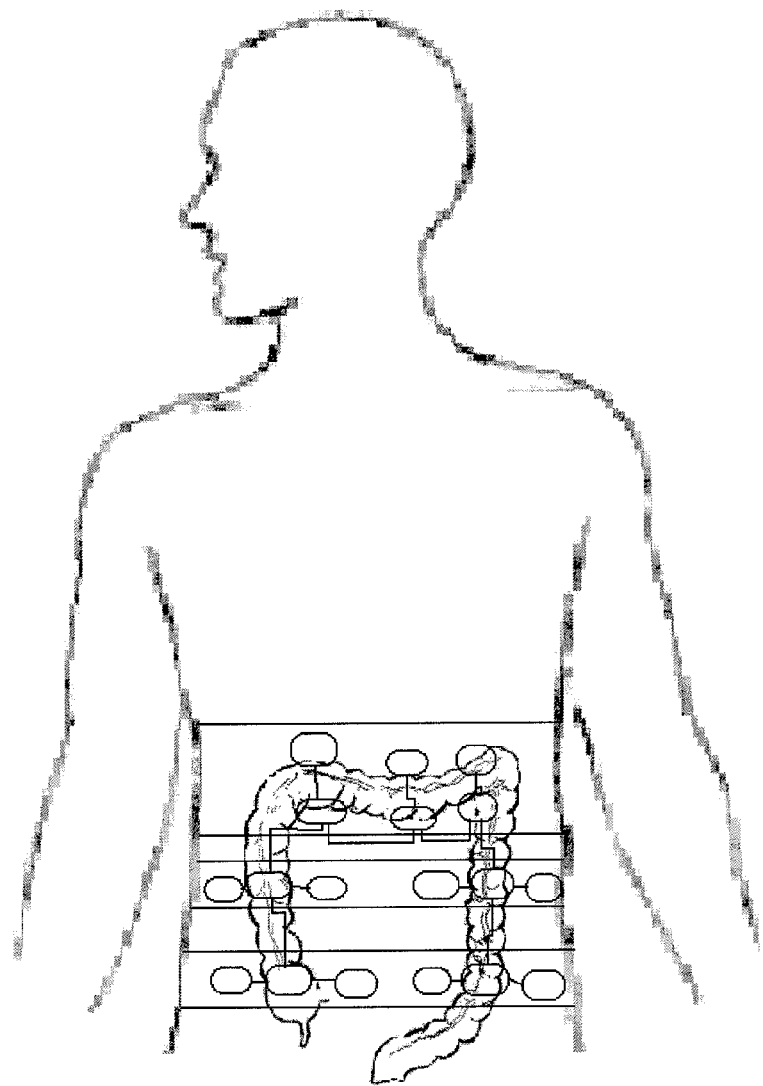
Figure 12E:
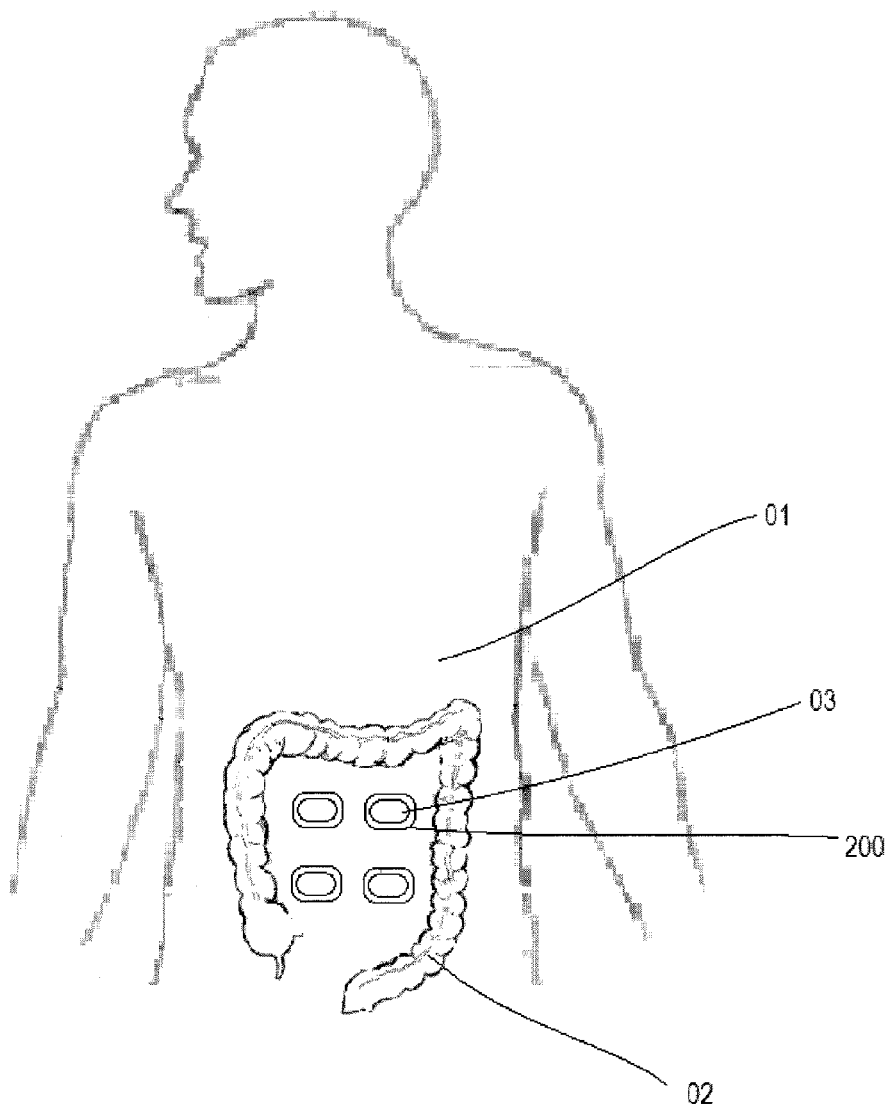

As the capsule camera travels through the GI tract by peristalsis, the capsule camera may not orient along a longitudinal direction of the GI tract. Furthermore, the patient's GI tract has different shapes along its length, at different locations and positions, which vary with the subject's motion or body pose. Both the required antenna orientation and the body tissue through which the wireless signal has to penetrate to reach the receiving unit are also constantly changing. The multi-path signals reflected through different tissues and bones will also be changing. Therefore, FIGS. 12A-D show some receiving unit placements that achieve better overall error rate performance. FIG. 12E is an example in which the antenna design is efficient or its power may be increased, so that the antenna placement is less restricted. Consequently, the antenna may be placed where it provides greater comfort to the patient and easier installation. In this embodiment, tape 200 fixes receiving unit 03 in place.

The detailed description above is provided to illustrate specific embodiments of the present invention and is not intended to be limiting. Numerous variations and modifications within the scope of the present invention are possible. The present invention is set forth in the following claims.

We claim:

1. A receiver system for receiving image data from a capsule camera, comprising:
    a plurality of receiving units each comprising:
        an antenna for receiving a signal transmitted wirelessly from the capsule camera;
        a receiver circuit coupled to the antenna that (a) processes the signal received in the antenna to recover data encoded therein; (b) generates information indicative of a parameter of the received signal and (c) outputs a digital signal comprising digital data encoding the recovered data and the parameter of the received signal; and
        an interface receiving the digital data from the receiver circuit for connecting to a processing circuit that recovers the image data from the digital data, wherein the receiving unit operates in an active mode and an inactive mode, the receiving unit being put into the active mode according to a network signal condition detected at a second receiving unit in the active mode within a predetermined distance of the receiving unit, and the parameter of the received signal being indicative of the network signal condition at the time the signal is received into the receiving unit; and
    wherein the processing circuit couples to the interfaces of the receiving units to receive from each coupled interface the digital data output from the receiver circuit associated with the coupled interface.

2. A receiver system as in claim 1, further comprises an archival memory for storing the digital data received into each receiving unit.

3. A receiver system as in claim 1, wherein each receiver circuit comprising a processor unit for controlling the operation of the receiving unit.

4. A receiver system as in claim 1, wherein the recovered data comprises image data.

5. A receiver system as in claim 1, wherein the digital data output from the receiver circuits are each divided into blocks substantially synchronized in time across the receiving units, the processing circuit selects a block from the substantially synchronized blocks of the receiving units.

6. A receiver system as in claim 5, wherein each receiving unit records a timestamp in the blocks it generates.

7. A receiver system as in claim 5, wherein the capsule camera transmits a timestamp at predetermined intervals.

8. A receiver system as in claim 5, wherein the substantially synchronized blocks are synchronized to within one half a duration of the substantially synchronized blocks.

9. A receiver system as in claim 5, wherein the block is selected according weightings assigned to the receiving units.

10. A receiver system as in claim 5, wherein the processing circuit selects the block according to the network signal conditions of the substantially synchronized blocks.

11. A receiver system as in claim 10, wherein the digital data is further divided into decoding intervals, each decoding interval spanning one or more of the synchronized blocks.

12. A receiver system as in claim 11 wherein, during a given decoding interval, the processing circuit selects a plurality of blocks, each selected block being selected from the substantially synchronized blocks within the given decoding interval.

13. A receiver system as in claim 12, wherein the selected blocks are contiguous in time spanning the decoding interval.

14. A receiver system as in claim 13, wherein the processing circuit perform decoding of the digital signal to select the image data.

15. A receiver system as in claim 14 wherein, when the processing circuit encounters a decoding error in a selected block, the processing circuit substitutes the selected block by another block in the substantially synchronized blocks from which the selected block was first selected.

16. A receiver system as in claim 11 wherein, when the processor circuit discovers that a bit length of the digital data in the decoding interval is other than an expected value, the processing circuit substitutes one of the selected blocks, the substituted selected block being the block corresponding to the block in the selected blocks having the least favorable network signal condition among the network conditions associated with the selected blocks.

17. A receiver system as in claim 1, wherein the block selection takes into consideration only blocks transmitted from receiving units operating in the active mode.

18. A receiver system as in claim 17, wherein the receiving units are put into active mode also according to an expected arrival time model for the capsule camera to travel in a human gastrointestinal tract.

19. A receiver system as in claim 17, wherein the parameter of the received signal further comprises a value representative of the time at which the signal is received into the receiving unit.

20. A receiver system as in claim 1, wherein the predetermined distance is a function of whether the receiving unit is located in a forward direction or located in a backward direction relative to the second receiving unit.

21. A receiver system as in claim 1 wherein the inactive mode comprises a power-saving mode.

22. A method for receiving image data from a capsule camera, comprising:
    providing a plurality of receiving units each comprising:
        an antenna for receiving a signal transmitted wirelessly from the capsule camera; a receiver circuit coupled to the antenna that (a) processes the signal received in the antenna to recover data encoded therein; (b) generates information indicative of a parameter of the received signal and (c) outputs a digital signal comprising digital data encoding the recovered data and the parameter of the received signal; and
        an interface receiving the digital data from the receiver circuit for coupling a processing circuit that recovers the image data from the digital data, wherein the receiving unit operates in an active mode and an inactive mode, the receiving unit being put into the active mode according to a network signal condition detected at a second receiving unit in the active mode within a predetermined distance of the receiving unit, and the parameter of the received signal being indicative of the network signal condition at the time the signal is received into the receiving unit;

coupling the processing circuit to the interfaces of the receiving units; and from each coupled interface, receiving into the processing circuit the digital data output from the receiver circuit associated with the coupled interface.

23. A method as in claim 22, wherein the receiving unit further comprises an archival memory for storing the digital data received into each receiving unit.

24. A method as in claim 22, wherein each receiver circuit further comprises a processor unit for controlling the operation of the receiving unit.

25. A method as in claim 22, wherein the recovered data comprises image data.

26. A method as in claim 22, wherein the digital data output from the receiver circuits are each divided into blocks substantially synchronized in time across the receiving units, the processing circuit selects a block from the substantially synchronized blocks of the receiving units.

27. A method as in claim 26, wherein each receiving unit records a timestamp in the blocks it generates.

28. A method as in claim 26, wherein the capsule camera transmits a timestamp at predetermined intervals.

29. A method as in claim 26, wherein the substantially synchronized blocks are synchronized to within one half a duration of the substantially synchronized blocks.

30. A method as in claim 26, wherein the block is selected according weightings assigned to the receiving units.

31. A method as in claim 26, wherein the block selection takes into consideration only blocks transmitted from receiving units operating in the active mode.

32. A method as in claim 31, further comprising putting one of the receiving units into active mode according to an expected arrival time model for the capsule camera to travel in a human gastrointestinal tract.

33. A method as in claim 31, wherein the parameter of the received signal further comprises a value representative of the time at which the signal is received into the receiving unit.

34. A method as in claim 26, wherein the block selection circuit selects the block according to the network signal conditions of the substantially synchronized blocks.

35. A method as in claim 34, wherein the digital data is further divided into decoding intervals, each decoding interval spanning a plurality of the substantially synchronized blocks.

36. A method as in claim 35 wherein, during a given decoding interval, the block selection circuit selects a plurality of blocks, each selected block being selected from the substantially synchronized blocks within the given decoding interval.

37. A method as in claim 36, wherein the selected blocks are contiguous in time spanning the decoding interval.

38. A method as in claim 36, wherein the processing circuit performs decoding of the digital signal to select the image data.

39. A method as in claim 38 wherein, when the processing circuit encounters a decoding error in a selected block, the processing circuit substitutes the selected block by another block in the substantially synchronized blocks from which the selected block was first selected.

40. A method as in claim 38 wherein, when the processor circuit discover that a bit length of the digital data in the decoding interval is other than an expected value, the processing circuit substitutes one of the selected blocks, the substituted selected block being the block corresponding to the block in the selected blocks having the least favorable network signal condition among the network conditions associated with the selected blocks.

41. A method as in claim 22, wherein the predetermined distance is a function of whether the receiving unit is located in a forward direction or located in a backward direction relative to the second receiving unit.

42. A method as in claim 22, wherein the inactive mode comprises a power-saving mode.

* * * * *